United States Patent [19]

Donovan

[11] Patent Number: 5,113,941
[45] Date of Patent: May 19, 1992

[54] SURFACE SAND DETECTION MONITORING DEVICE AND METHOD

[75] Inventor: Joseph F. Donovan, Spring, Tex.

[73] Assignee: Baker Hughes Incorporated, Houston, Tex.

[21] Appl. No.: 610,356

[22] Filed: Nov. 7, 1990

[51] Int. Cl.$^5$ .............. E21B 43/34; E21B 47/00
[52] U.S. Cl. .................. 166/250; 73/155; 73/863.23; 166/75.1; 166/113; 210/323.2
[58] Field of Search .............. 166/250, 113, 91, 75.1, 166/379; 73/863.23, 61 R, 863.31, 151, 155; 210/323.2, 85, 93

[56] References Cited

U.S. PATENT DOCUMENTS

| | | | |
|---|---|---|---|
| T939,012 | 10/1975 | Baldwin | 73/61 R |
| 3,407,572 | 10/1968 | Tolley | 55/283 |
| 3,726,066 | 4/1973 | Colley et al. | 55/302 |
| 3,793,811 | 2/1974 | Bourne | 55/294 |
| 3,816,773 | 6/1974 | Baldwin et al. | 73/61 R X |
| 3,841,144 | 10/1974 | Baldwin | 73/61 R |
| 3,854,323 | 12/1974 | Hearn et al. | 73/155 X |
| 4,060,130 | 11/1977 | Hart | 166/312 |
| 4,106,562 | 8/1978 | Barnes et al. | 166/75.1 X |
| 4,398,931 | 8/1983 | Shevlin | 55/341 R |
| 4,445,912 | 5/1984 | Volk et al. | 55/283 |
| 4,456,061 | 6/1984 | Swift, Jr. et al. | 166/75.1 |
| 4,704,210 | 11/1987 | Boze et al. | 210/323.2 X |
| 4,856,591 | 8/1989 | Donovan et al. | 166/278 |
| 4,858,691 | 8/1989 | Ilfrey et al. | 166/278 |
| 4,917,183 | 4/1990 | Gaidry et al. | 166/278 |

Primary Examiner—Hoang C. Dang
Attorney, Agent, or Firm—Charles D. Gunter, Jr.

[57] ABSTRACT

A method and device are shown for monitoring the level of particulate matter in a stream of hydrocarbons produced from a well bore. A downstream filter is installed within a surface conduit which communicates with the production conduit for trapping particulate matter in the stream of hydrocarbons passing within the surface conduit. The contents of the downstream filter are sampled over predetermined intervals to determine information regarding the type and amount of particulate matter trapped. The production rate of produced hydrocarbons is adjusted based upon the information gathered.

12 Claims, 2 Drawing Sheets

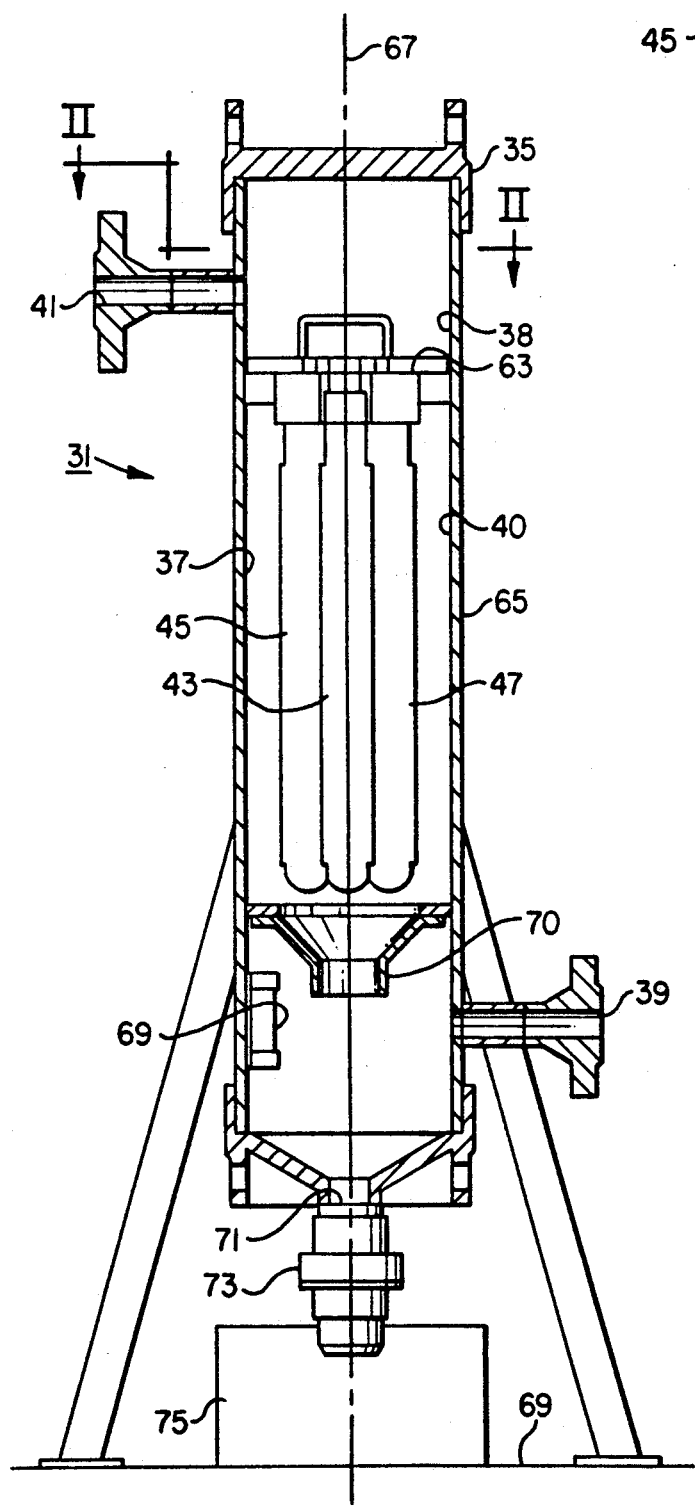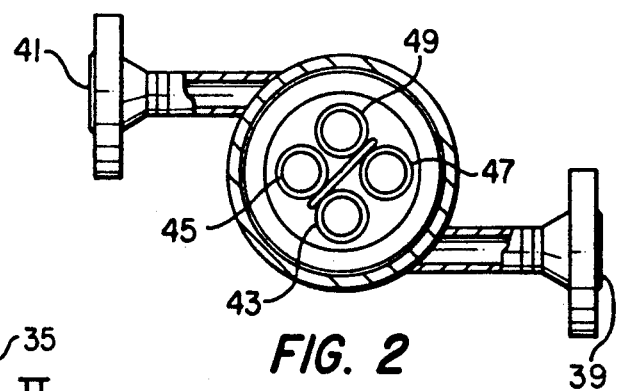
FIG. 1
FIG. 2

SURFACE SAND DETECTION MONITORING DEVICE AND METHOD

BACKGROUND OF THE INVENTION

1. Field of the Invention

The present invention relates to a method and device for monitoring the level of particulate matter in a stream of hydrocarbons which are being produced from a well bore and, specifically, to a surface sand detection monitor for monitoring the type and amount of sand in a stream of hydrocarbons being produced at the well surface.

2. Description of the Prior Art

As oil and gas wells are being drilled through formations which generally are of an unconsolidated nature, the produced fluids can be expected to contain particulate matter, referred to herein as "sand." It is undesirable to produce particulate matter above a certain level with production fluids, because such production results in abrasion of the production tubing, valves and other equipment used to produce the well, as well as the equipment used to carry such fluids from the well. Unacceptable levels of sand in the production fluids can actually result in blockage of the production tubing, thereby halting fluid production altogether.

A variety of devices are known in the art for reducing the production of sand which involve "gravel packing" the well during completion operations. Gravel packing operations typically include the installation of a device on the production conduit or tubular work string which includes a slotted or ported cylindrically shaped member. This member is designed to prevent the passage of solid particles exceeding a predetermined size therethrough and into the interior of the production conduit. In a typical operation, gravel packing is introduced into an annular area between the production conduit or work string and the casing of the well or, in the event of a non-cased well, the well bore wall. The gravel used as the packing medium is deposited longitudinally along the exterior of the slotted or ported cylindrical member.

Gravel packing devices are shown, for example, in U.S. Pat. No. 4,856,591, issued Aug. 15, 1989, to Donovan et al. and U.S. Pat. No. 4,858,691, issued Aug. 22, 1989, to Ilfrey et al., both assigned to the assignee of the present invention.

Typically, after a well is completed, the flow of production fluids are routed through the production tubing in the well bore and through a surface conduit to a desired surface location which could be, for example, an oil and gas separator unit. The production flow rate is typically controlled by means of a "choke", or regulator, located in the surface conduit upstream of the oil and gas separator unit and other related surface equipment. The choke includes an interchangeable orifice so that the flow rate of the produced fluids can be varied by interchanging orifices of different diameter. By properly selecting the flow rate of the produced fluids, sanding problems can be greatly reduced or eliminated.

It is an object of the present invention to provide a surface sand detection monitor in the surface conduit to provide information regarding the type and amount of sand being produced with the production fluids. Using this information, the flow rate of the produced fluids can be adjusted by adjusting the production flow regulator, as required, to minimize sand production.

It is also an object of the invention to provide a method of monitoring the level of sand in a stream of hydrocarbons which are being produced from a well bore in order to provide an indication of the appropriate time for installing or activating gravel packing devices and methods to prevent problems caused by excess sand in the produced fluids.

Another object of the invention is to provide such a surface sand detection monitor which can be utilized to provide information regarding the type and amount of sand in the produced fluids without requiring that the well be shut-in at any point in the information gathering process.

SUMMARY OF THE INVENTION

The method of the invention is used to monitor the level of sand in a stream of hydrocarbons which are being produced from a well bore through a production conduit located in the well bore and through a surface conduit to a desired surface location. Monitoring is accomplished by installing a downstream filter unit within the surface conduit at the well surface for trapping sand in the stream of hydrocarbons passing within the surface conduit. The contents of the downstream filter unit are sampled over predetermined intervals to determine information regarding the type and amount of sand trapped. The production rate of produced hydrocarbons is then adjusted based upon the information gathered.

Preferably, the surface conduit is provided with a flow control regulator for controlling the flow rate of hydrocarbons being produced through the production conduit. A pair of downstream filter units can be installed at the well surface and arranged in parallel fashion in communication with the surface conduit at the well surface for trapping sand in the stream of hydrocarbons passing within the surface conduit. Each downstream filter unit comprises a high pressure vessel with an interior, an inlet, and an outlet for connecting the filter unit within the flow path of the surface conduit. A filter element is located within the interior of each high pressure vessel for filtering sand in the stream of hydrocarbons passing through the surface conduit to the respective vessel inlet and through the vessel interior to the respective vessel outlet. Each high pressure vessel also has a sample port to allow the filtered sand to be sampled, to thereby provide an indication of the optimal production rate for produced hydrocarbons.

Valve means associated with each of the pair of downstream filter units are provided for independently controlling the flow of produced hydrocarbons through each of the filter units in the pair. By closing off flow through one of the filter units in the pair while allowing flow to continue through the other of the filter units in the pair, the contents of the downstream filter unit which has been closed off can be sampled over a predetermined interval to determine the needed information while allowing flow to continue through the other of the filter units in the pair. By alternating the sampling step between each of the downstream filter units in the filter unit pair, the required information can be gathered without shutting-in the well.

The filter element located within each downstream filter unit can include at least one pre-packed gravel packing screen in which a selected particulate material is disposed between an outer member and an inner ported member to prevent sand produced with the hydrocarbon stream from passing through the filter element and out the vessel outlet.

In one embodiment, the high pressure vessel is designed as an elongate housing with a longitudinal axis which is arranged generally vertical to the well surface, the vessel inlet and vessel outlets being located at opposite extents of the elongate housing generally perpendicular to the longitudinal axis thereof. A replaceable coupon, mounted in alignment with the vessel inlet, absorbs the impact of the entering stream of hydrocarbons entering the vessel interior from the surface conduit.

Additional objects, features and advantages will be apparent in the written description which follows.

BRIEF DESCRIPTION OF THE DRAWINGS

FIG. 1 is a plan view of the surface sand detection monitor used in the method of the invention, partially in cross-section;

FIG. 2 is a cross-sectional view taken along lines II.—II. in FIG. 1;

in FIG. 4.

DETAILED DESCRIPTION OF THE INVENTION

Figure 3:
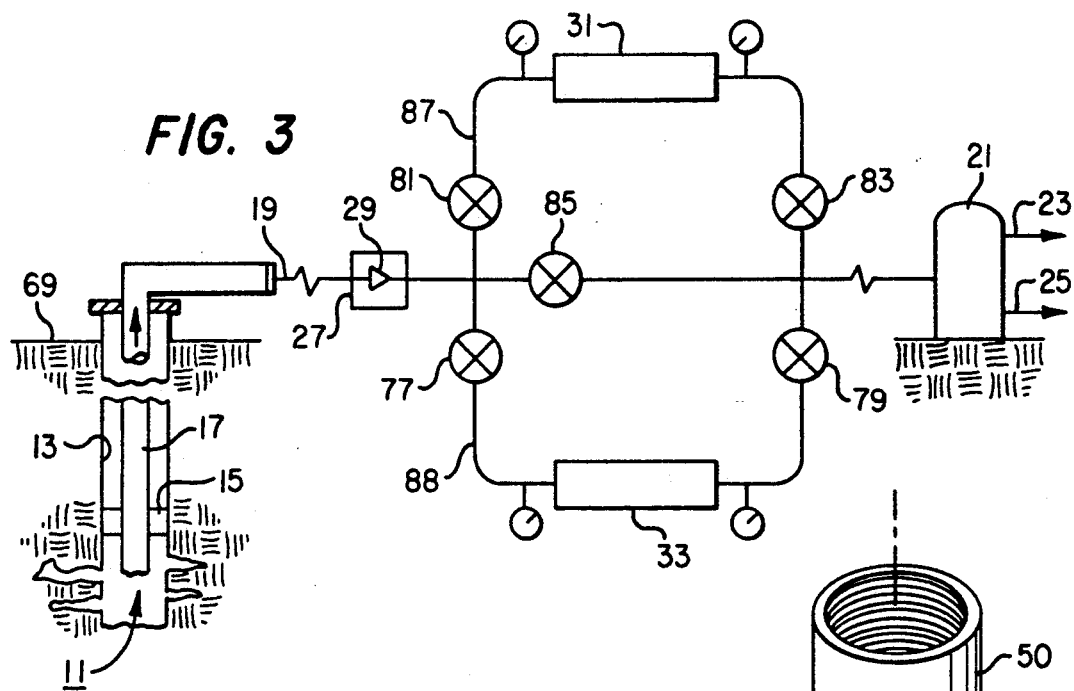
FIG. 3 is a simplified, schematic view of the method of the invention showing a pair of surface sand detection monitors mounted in parallel fashion within the surface conduit.

Turning first to FIG. 3, there is shown a longitudinally sectioned schematic illustration of a well bore 11 having a casing string 13 cemented therein. A packer 15 is carried on a work or production conduit 17. The production conduit 17 communicates with a surface conduit (illustrated schematically as 19 in FIG. 3) for transporting a stream of hydrocarbons to a desired surface location such as an oil and gas separator unit 21 having a gas outlet line 23 and an oil outlet conduit 25. The surface conduit 19 also has installed therein a "choke" 27 which includes an interchangeable orifice 29 which serves as a flow control regulator, wherein the production rate of produced hydrocarbons can be controlled by changing the size of the orifice 29 in the choke 27 at the well surface. These elements will all be familiar to those skilled in the oil and gas well production arts and do not form a part of the present invention.

Illustrated schematically in FIG. 3 are two downstream filter units 31, 33 which serve as surface sand detection monitors. The filter units 31, 33 are arranged in parallel fashion within the surface conduit 19 upstream of the oil and gas separator unit 21. Although the choke 27 is shown located upstream of the filter units 31, 33, it will be understood that, for purposes of the present invention, the choke 27 could be located downstream of the filter units 31, 33, as well. Alternatively, filter units could be installed on either side of the choke 27.

FIG. 1 shows one of the filter units 31 which is adapted for monitoring the level of particulate matter, i.e. sand, in a stream of hydrocarbons which are being produced from the well bore 11 through the production conduit 17 and through the surface conduit 19 to a desired surface location. The desired surface location could be, for example, the oil and gas separator unit 21 (FIG. 3). The downstream filter unit is comprised of a high pressure vessel 35 having an interior 37, an inlet 39 and an outlet 41 for connection within the surface conduit 19. A plurality of filter elements 43, 45, 47, 49 are located within the interior 37 of the high pressure vessel 35 for filtering sand in the stream of hydrocarbons passing through the surface conduit 19 to the vessel inlet 39 and through the vessel interior 37 to the vessel outlet 41. The filter elements are mounted within the vessel interior 37 on a flange 63 (FIG. 1) which divides the interior into an upper compartment 38 and a lower compartment 40.

By "high pressure" is meant that the vessel and filter elements will typically be exposed to pressures on the order of 1,500 psi when mounted downstream of the choke 27 and pressures ranging as high as about 10,000 psi if mounted upstream of the choke 27.

The filter element component of each filter unit 31, 33 can be any filter means capable of filtering the particulate matter in the hydrocarbon stream while effectively withstanding the physical environment of the intended application Thus, a variety of filtering materials can be utilized which can be mounted in rigid fashion within the vessel interior. For instance, suitable screen means including stainless steel mesh screen, wrapped steel wire screens made of plain steel wire or an alloy of non-ferrous wire such as steel, stainless steel, copper, high brass, commercial bronze, phosphor, monel, nickel, aluminum, or combinations thereof can be utilized. The filter element can also be manufactured of a number of special alloys including pure iron, high brass, phosphor bronze, pure nickel and the like. It may be provided in a coated or uncoated form. In some instances, it may be desirable to coat the mesh with chemical compounds, such as corrosion inhibitors or other chemical protective combinations. The filter element may be provided in the form of any one of a number of weaves or crimps.

Preferably, the filter elements 43, 45, 47, 49 include at least one pre-packed gravel packing screen in which a selected particulate material is disposed between an outer member and an inner ported member to prevent sand and other particulate matter produced with the hydrocarbon stream from passing out the vessel outlet 41. A preferred pre-packed gravel packing screen is described in U.S. Pat. No. 4,917,183, issued Apr. 17, 1990, to John E. Gaidry, et al. assigned to the assignee of the present invention, the disclosure of which is incorporated herein by reference.

Figure 5:
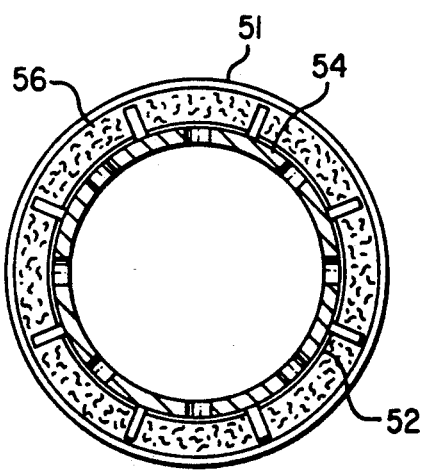
FIG. 5 is a cross-sectional view taken along lines V.—V.
Figure 4:
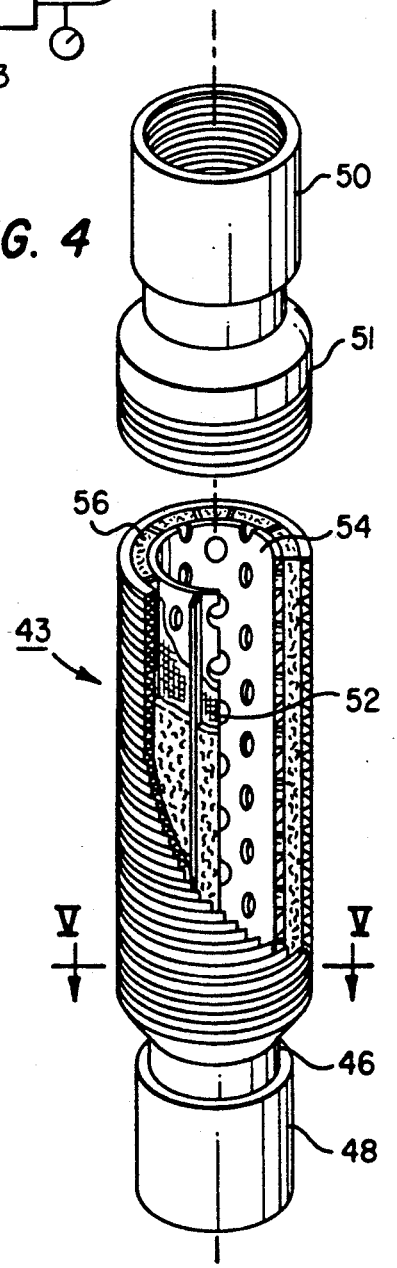
FIG. 4 is an isolated view, partially in cross-section and partially broken away of a pre-packed gravel packing screen used as the filter element in the device of FIG. 1.

FIG. 4 is an isolated view of one of the filter elements 43. Preferably, the filter element 43 is a pre-packed gravel packing screen as described in U.S. Pat. No. 4,917,183, previously incorporated by reference. The element 43 includes upper and lower tubular portions 46, 51, portion 51 forming an open end 50 and portion 46 being closed off by an end cap 48. An inner wire mesh 52 overlays an inner ported mandrel 54. A selected particulate material (56 in FIG. 5) is disposed between the inner wire mesh 52 and an outer wrapped screen 56. The filter elements 43 can be secured within the vessel by any convenient technique. In this case, the elements 43, 45, 47 and 49 are secured by threading the upper tubular portions 50 to the flange 63 (FIG. 1). The filter elements serve to prevent sand in the produced hydrocarbons from passing from the lower chamber 40 of the filter unit 31 to the upper chamber 38.

FIG. 1 shows the high pressure vessel 35 in greater detail. The vessel 35 includes an elongate housing 65 with a longitudinal axis 67 which is arranged generally vertical to the well surface (69 in FIG. 3). In the embodiment of the invention illustrated in FIG. 1, the vessel inlet 39 and vessel outlet 41 are located at opposite extents of the elongate housing 65 generally perpendicular to the longitudinal axis 67 Preferably, the vessel interior 37 includes a replaceable coupon 69 mounted within the vessel interior 37 in alignment with the vessel inlet 39 for absorbing the impact of the entering stream of hydrocarbons entering the vessel interior from the surface conduit. The hydrocarbon stream can contain gas, oil or water and, typically, will contain all three.

The high pressure vessel 35 also has a sample port 71 at the lower extent thereof which communicates through a dump valve 73 with a sample container 75. The collected material is sampled, to thereby provide an indication of the optimal production rate for the produced hydrocarbons.

As shown in FIG. 3, there are preferably at least two filter units 31, 33 of the invention arranged in a parallel circuit with the surface conduit 19. Valve means, associated with each of the pair of filter units 31, 33 independently control the flow of produced hydrocarbons through each of the filter units in the pair. Thus, valves 77, 79 control flow through the downstream filter unit 33 while valves 81, 83 control the flow through downstream filter unit 31. By closing valves 77, 79, 81, 83 and opening valve 85, flow can proceed directly through the surface conduit 19 to the oil and gas separator 21 without passing through either of the downstream filter units. By closing valves 77, 79, 85 and opening valves 81, 83, flow is diverted through the branch conduit 87 and through downstream filter unit 31 on its way to the separator unit 21. By closing valves 81, 83, 85 and opening valves 77, 79, flow is diverted through branch conduit 88 to the downstream filter unit 33 on the way to the separator unit 21.

The method of the invention is used to monitor the level of particulate matter, such as sand, in a stream of hydrocarbons which are being produced from a well bore 11 through a production conduit 17 located in the well bore and through a surface conduit 19 to a desired surface location such as the oil and gas separator unit 21 located at the well surface.

In the preferred arrangement of FIG. 3, a pair of downstream filter units 31, 33 are installed at the well surface 69 arranged in parallel fashion within the surface conduit 19 either upstream, downstream or on both sides of the flow control regulator 27 for trapping particulate matter in the stream of hydrocarbons passing within the surface conduit 19. The valves 77, 79, 81, 83, 85 associated with each of the pair of downstream filter units 31, 33 are used to independently control the flow of produced hydrocarbons through each of the filter units 31, 33 in the pair, as previously described. Thus, one of the filter units 31, 33 is typically closed off while allowing flow to continue through the other of the filter units in the pair. The contents of the downstream filter unit which has been closed off is sampled over a predetermined interval to determine needed information regarding the amount and type of particulate matter, while allowing flow to continue through the other of the filter units in the pair.

The flow control regulator 27 is then adjusted at the well surface to control the production rate of produced hydrocarbons based upon the information gathered regarding the amount and type of particulate matter trapped in the sample container 75. The sampling step can be alternated between each of the downstream filter units 31, 33 in the pair by alternating the valve means, so that it is not necessary to shut-in the well at any point in the sampling operation.

The present invention provides several advantages not present in the prior art. By using the downstream filter units as surface sand detection monitors, it is possible to adjust the production flow rate to an optimum value whereby particulate matter in the produced fluids does not exceed acceptable limits. By reducing and controlling the level of particulate matter, equipment life is prolonged and well shut-ins are avoided. In addition to optimizing the production flow rate to control sand production, the device and method of the invention provide valuable information concerning the type and amount of particulates produced. This information gives valuable insight into the nature of the subterranean formation and provides advance warning of the need for more extensive gravel packing operations.

While the invention has been shown in only one of its forms, it is not thus limited but is susceptible to various changes and modifications without departing from the spirit thereof.

I claim:

1. A method of monitoring the level of particulate matter in a stream of hydrocarbons which are being produced from a well bore, through a production conduit located in the well bore, and through a surface conduit to an oil and gas separator unit located at the well surface, the surface conduit being provided with a flow control regulator for controlling the flow rate of hydrocarbons being produced through the production conduit, the method comprising the steps of:

installing a downstream filter unit within the surface conduit at the well surface upstream of the oil and gas separator unit for trapping particulate matter in the stream of hydrocarbons passing within the surface conduit, the downstream filter unit including a high pressure vessel with an interior, an inlet and an outlet for connection within the surface conduit, and wherein a filter element is located within the interior of the high pressure vessel for filtering particulate matter in the stream of hydrocarbons passing through the surface conduit to the vessel inlet and through the vessel interior to the vessel outlet;

sampling the contents of the downstream filter unit over predetermined intervals by removing trapped particulate matter to determine information regarding the amount of particulate matter trapped;

adjusting the flow control regulator at the well surface to control the production rate of produced hydrocarbons based upon the information gathered regarding the amount of particulate matter trapped.

2. The method of claim 1, wherein the production rate is decreased as the amount of particulate matter sampled increases above a predetermined level and the production rate is increased when the amount of particulate matter sampled falls below a predetermined level.

3. The method of claim 2, wherein the flow control regulator is a choke which includes an interchangeable orifice, and wherein the production rate of produced hydrocarbons is controlled by changing the size of the orifice in the choke.

4. A method of monitoring the level of particulate matter in a stream of hydrocarbons which are being produced from a well bore, through a production conduit located in the well bore, and through a surface conduit to an oil and gas separator unit located at the well surface, the surface conduit being provided with a flow control regulator for controlling the flow rate of hydrocarbons being produced through the production conduit, the method comprising the steps of:

installing a pair of downstream filter units at the well surface, the pair of filter units being arranged in parallel fashion with the surface conduit at the well surface upstream of the oil and gas separator unit for trapping particulate matter in the stream of hydrocarbons passing within the surface conduit each downstream filter unit including a high pressure vessel with an interior, an inlet and an outlet for connection within the surface conduit, and wherein a filter element is located within the interior of each high pressure vessel for filtering particulate matter in the stream of hydrocarbons passing through the surface conduit to the respective vessel inlet and through the vessel interior to the respective vessel outlet;

providing valve means associated with each of the pair of downstream filter units for independently controlling the flow of produced hydrocarbons through each of the filter units in the pair;

closing off flow through one of the filter units in the pair while allowing flow to continue through the other of the filter units in the pair;

sampling the contents of the downstream filter unit which has been closed off over a predetermined interval by removing trapped particulate matter to determine information regarding the amount of particulate matter trapped while allowing flow to continue through the other of the filter units in the pair;

adjusting the flow control regulator at the well surface to control the production rate of produced hydrocarbons based upon the information gathered regarding the amount of particulate matter trapped.

5. The method of claim 4, further comprising the steps of:

alternating the sampling step between each of the downstream filter units in the filter unit pair by alternating the valve means.

6. A surface sand detection monitor adapted for monitoring the level of particulate matter in a stream of hydrocarbons which are being produced from a well bore, through a production conduit located in the well bore, and through a surface conduit to a desired surface location, the monitor comprising:

a downstream filter unit located within the surface conduit at the well surface for trapping particulate matter in the stream of hydrocarbons passing within the surface conduit, the downstream filter unit including a high pressure vessel with an interior, an inlet and an outlet for connection within the surface conduit, and wherein a filter element is located within the interior of the high pressure vessel for filtering particulate matter in the stream of hydrocarbons passing through the surface conduit to the vessel inlet and through the vessel interior to the vessel outlet;

wherein the high pressure vessel has a sample port to allow the filtered particulate matter to be sampled, to thereby provide an indication of the optimal production rate for the produced hydrocarbons;

wherein the high pressure vessel includes an elongate housing with a longitudinal axis which is arranged generally vertical to the well surface and wherein the vessel inlet vessel outlets are located at opposite extents of the elongate housing generally perpendicular to the longitudinal axis; and wherein the vessel interior includes a replaceable coupon mounted in alignment with the vessel inlet for absorbing the impact of the entering stream of hydrocarbons entering the vessel interior from the surface conduit.

7. The surface sand detection monitor of claim 6, wherein a plurality of pre-packed gravel packing screens are mounted within the vessel interior, each pre-packed gravel packing screen having a longitudinal axis which is arranged generally parallel to the longitudinal axis of the vessel housing.

8. A surface sand detection monitor adapted for monitoring the level of particulate matter in a stream of hydrocarbons which are being produced from a well bore, through a production conduit located in the well bore, and through a surface conduit to an oil and gas separator unit located at the well surface, the surface conduit being provided with a flow control regulator for controlling the flow rate of hydrocarbons being produced through the production conduit to obtain an optimal flow rate, the monitor comprising:

a downstream filter unit located within the surface conduit at the well surface upstream of the oil and gas separator unit for trapping particulate matter in the stream of hydrocarbons passing within the surface conduit, the downstream filter unit including a high pressure vessel with an interior, an inlet and an outlet for connection within the surface conduit, and wherein a filter element is located within the interior of the high pressure vessel for filtering particulate matter in the stream of hydrocarbons passing through the surface conduit to the vessel inlet and through the vessel interior to the vessel outlet;

wherein the high pressure vessel has a sample port to allow the filtered particulate matter to be sampled, to thereby provide an indication of the optimal production rate for the produced hydrocarbons;

wherein the filter element located within the downstream filter unit includes at least one pre-packed gravel packing screen in which a selected particulate material is disposed between an outer member and an inner ported member to prevent sand produced with the hydrocarbon stream from passing out the vessel outlet; and wherein the high pressure vessel includes an elongate housing with a longitudinal axis which is arranged generally vertical to the well surface and wherein the vessel inlet and vessel outlets are located at opposite extents of the elongate housing generally perpendicular to the longitudinal axis.

9. The surface sand detection monitor of claim 8, wherein a plurality of pre-packed gravel packing screens are mounted within the vessel interior, each pre-packed gravel packing screen having a longitudinal axis which is arranged generally parallel to the longitudinal axis of the vessel housing.

10. The surface sand detection monitor of claim 8, further comprising:

a pair of downstream filter units connected by associated conduit in parallel fashion within the surface conduit at the well surface;

valve means associated with each of the pair of downstream filter units for independently controlling the flow of produced hydrocarbons through each of the filter units in the pair.

11. The surface sand detection monitor of claim 8, wherein the flow control regulator is a choke which includes an interchangeable orifice, and wherein the production rate of produced hydrocarbons is controlled by changing the size of the orifice in the choke.

12. A surface sand detection monitor adapted for monitoring the level of particulate matter in a stream of hydrocarbons which are being produced from a well bore, through a production conduit located in the well bore, and through a surface conduit to an oil and gas separator unit located at the well surface, the surface conduit being provided with a flow control regulator for controlling the flow rate of hydrocarbons being produced through the production conduit to obtain an optimal flow rate, the monitor comprising:

a downstream filter unit located within the surface conduit at the well surface upstream of the oil and gas separator unit for trapping particulate matter in the stream of hydrocarbons passing within the surface conduit, the downstream filter unit including a high pressure vessel with an interior, an inlet and an outlet for connection within the surface conduit, and wherein a filter element is located within the interior of the high pressure vessel for filtering particulate matter in the stream of hydrocarbons passing through the surface conduit to the vessel inlet and through the vessel interior to the vessel outlet;

wherein the high pressure vessel has a sample port to allow the filtered particulate matter to be sampled, to thereby provide an indication of the optimal production rate for the produced hydrocarbons;

wherein the filter element located within the downstream filter unit includes at least one pre-paced gravel packing screen in which a selected particulate material is disposed between an outer member and an inner ported member to prevent sand produced with the hydrocarbon stream from passing out the vessel outlet;

wherein the high pressure vessel includes an elongate housing with a longitudinal axis which is arranged generally vertical to the well surface and wherein the vessel inlet and vessel outlets are located at opposite extents of the elongate housing generally perpendicular to the longitudinal axis; and wherein the vessel interior includes a replaceable coupon mounted in alignment with the vessel inlet for absorbing the impact of the entering stream of hydrocarbons entering the vessel interior from the surface conduit.

* * * * *